United States Patent
Alissa et al.

(10) Patent No.: US 10,921,300 B2
(45) Date of Patent: Feb. 16, 2021

(54) INTERNAL SERVER AIR QUALITY STATION

(71) Applicant: Microsoft Technology Licensing, LLC, Redmond, WA (US)

(72) Inventors: Husam Alissa, Redmond, WA (US); Osvaldo P. Morales, Normandy Park, WA (US); Roy Medhi Zeighami, Fall City, WA (US); Brandon Aaron Rubenstein, Issaquah, WA (US); Scot Edward Heath, Issaquah, WA (US); Adolfo Bravo Ferreira, Poulsbo, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 187 days.

(21) Appl. No.: 16/161,044

(22) Filed: Oct. 15, 2018

(65) Prior Publication Data
US 2020/0116690 A1    Apr. 16, 2020

(51) Int. Cl.
*G01N 33/00* (2006.01)
*G01N 27/12* (2006.01)
(Continued)

(52) U.S. Cl.
CPC ......... *G01N 33/0031* (2013.01); *G01N 27/12* (2013.01); *G01N 27/121* (2013.01);
(Continued)

(58) Field of Classification Search
CPC .. G01N 33/0031; G01N 27/12; G01N 27/121; H05K 7/20172; H05K 1/0213;
(Continued)

(56) References Cited

U.S. PATENT DOCUMENTS

| | | | | |
|---|---|---|---|---|
| 2,458,048 A | * | 1/1949 | Bauman | F25D 17/042 |
| | | | | 62/176.6 |
| 3,039,355 A | * | 6/1962 | Suter | G01N 21/4133 |
| | | | | 356/37 |

(Continued)

FOREIGN PATENT DOCUMENTS

| | | |
|---|---|---|
| GB | 2516441 A | 1/2015 |
| JP | 57096244 A * | 6/1982 ........... G01N 27/121 |

OTHER PUBLICATIONS

Pandiyan, V., 2013. Development of Detailed Computational Flow Model of High End Server and Validation Using Experimental Methods. (Year: 2013).*

(Continued)

*Primary Examiner* — Christopher P Mcandrew
(74) *Attorney, Agent, or Firm* — Watson Patents, PLC; Vladan M. Vasiljevic

(57) ABSTRACT

Air quality inside a computing device is monitored utilizing an air quality monitor that can be sized to simulate a server computing device and can have multiple sensing equipment mounted inside, including equipment to detect corrosive aspects in the air and condensation sensing equipment to detect instances in which condensation can form on computing device hardware. Corrosion sensing can include metallic members that can be electrically coupled to voltage that can induce a current within the metallic members, thereby more accurately simulating the corrosion of operating PCBs. Condensation sensing can include condensation hosting members that can have a thermal mass that is approximately equal to the thermal mass of PCBs and can include heating elements by which the condensation hosting members can more accurately simulate the thermal effects and aspects of operating PCBs, and also moisture detectors, (Continued)

including electrical and optical moisture detectors. Additionally, an off-gassing chamber can be included.

20 Claims, 4 Drawing Sheets

(51) Int. Cl.
  *H05K 1/02* (2006.01)
  *H05K 7/14* (2006.01)
  *H05K 7/20* (2006.01)
(52) U.S. Cl.
  CPC ......... *H05K 1/0213* (2013.01); *H05K 7/1427* (2013.01); *H05K 7/20172* (2013.01); *H05K 7/20736* (2013.01); *H05K 2201/09218* (2013.01); *H05K 2201/10151* (2013.01)
(58) Field of Classification Search
  CPC ............. H05K 7/1427; H05K 7/20736; H05K 2201/10151; H05K 2201/09218
  USPC ........................................................ 324/694
  See application file for complete search history.

(56) References Cited

U.S. PATENT DOCUMENTS

| | | | | |
|---|---|---|---|---|
| 4,791,413 | A * | 12/1988 | Lyczek | G08B 21/20 340/604 |
| 6,126,312 | A * | 10/2000 | Sakai | G01N 27/121 324/664 |
| 6,285,198 | B1 * | 9/2001 | Nelson | A01D 41/1277 324/658 |
| 7,832,925 | B2 * | 11/2010 | Archibald | H05K 7/20609 374/29 |
| 9,278,303 | B1 | 3/2016 | Somani et al. | |
| 9,445,531 | B1 | 9/2016 | Heydari | |
| 10,299,408 | B1 | 5/2019 | Lachapelle | |
| 2003/0107385 | A1 * | 6/2003 | Shon | G01N 27/225 324/694 |
| 2006/0132785 | A1 * | 6/2006 | Fischer | G01N 21/47 356/445 |
| 2008/0036476 | A1 * | 2/2008 | Nielsen | G01N 17/02 324/700 |
| 2008/0304236 | A1 * | 12/2008 | Murakami | H05K 7/207 361/699 |
| 2010/0214557 | A1 * | 8/2010 | Akiyama | G01N 21/05 356/73 |
| 2011/0187393 | A1 * | 8/2011 | Vokey | G01N 27/048 324/694 |
| 2011/0210014 | A1 * | 9/2011 | Garosshen | G01N 27/121 205/776.5 |
| 2012/0313652 | A1 * | 12/2012 | Jaman | E04D 13/006 324/694 |
| 2013/0137357 | A1 | 5/2013 | Chang et al. | |
| 2013/0265064 | A1 * | 10/2013 | Hamann | G01N 17/04 324/700 |
| 2014/0167791 | A1 * | 6/2014 | Feyh | G01N 27/121 324/664 |
| 2015/0268152 | A1 * | 9/2015 | Friedersdorf | G01N 33/0031 73/25.01 |
| 2015/0346127 | A1 * | 12/2015 | Kalinichev | H02H 5/083 361/86 |
| 2015/0364940 | A1 * | 12/2015 | Bulur | H01M 10/4207 320/136 |
| 2016/0025665 | A1 * | 1/2016 | Hebert | G01N 27/223 324/664 |
| 2016/0033356 | A1 * | 2/2016 | DeAngelo | G01M 3/40 324/694 |
| 2016/0041085 | A1 * | 2/2016 | England | G01N 17/043 436/6 |
| 2016/0198593 | A1 * | 7/2016 | Schmitt | H05K 7/20836 361/679.49 |
| 2016/0362307 | A1 * | 12/2016 | Shiner | B01D 1/305 |
| 2017/0181328 | A1 * | 6/2017 | Shelnutt | H05K 7/20781 |
| 2018/0139870 | A1 * | 5/2018 | Meadows | F28D 1/0443 |
| 2018/0276914 | A1 * | 9/2018 | Villemin | F02D 41/222 |

OTHER PUBLICATIONS

Klein, L.J., Schappert, M. and Hamann, H.F., 2012, May. Corrosion risk management in IT facilities. In 13th InterSociety Conference on Thermal and Thermomechanical Phenomena in Electronic Systems (pp. 353-357). IEEE. (Year: 2012).*
English Translation of Abstract of JP357096244A (Year: 1982).*
"International Search Report and Written Opinion Issued in PCT Application No. PCT/US2019/054909", dated Jan. 7, 2020, 12 Pages.

* cited by examiner

INTERNAL SERVER AIR QUALITY STATION

BACKGROUND

Increasingly, a computing environment need not be supported by hardware that is physically co-located with a user utilizing such a computing environment, but rather can be supported by networked computing hardware aggregated into large data centers that are physically remote from the user. Often such computing environments are referred to as "cloud computing environments" and can provide users with different computing environments that are typically supported by virtual machines hosted by large collections of computing hardware providing stability, redundancy, and high availability.

A modern data center represents a large financial investment, both in computing device hardware, and also in the hardware providing the relevant support systems for such computing devices. For example, data centers often comprise climate control hardware, redundant power systems, physical security, and other like support systems, in addition to the computing device hardware itself, which, can comprise thousands of computing devices, storage devices, networking devices, and other like computing device hardware.

Because of the large quantities of computing device hardware housed in a typical data center, even small improvements in the reliability of such computing device hardware can mean thousands of fewer hardware failures per year, with attendant cost savings and service reliability improvements. In some instances, the reliability of computing device hardware can be negatively impacted by air quality and, conversely, improvements in air quality can increase the reliability of computing device hardware. Traditionally, however, data center air quality was measured only at the data center level, such as by air quality sensors installed externally to the computing devices themselves. Such externally positioned sensors, however, may not accurately identify the air quality within individual computing devices, and it is the air inside of the individual computing devices that can have the greatest impact on computing device hardware that is also housed inside of those individual computing devices.

SUMMARY

Air quality inside of a computing device, such as a typical rack-mounted blade server computing device in a data center, can be monitored utilizing an air quality monitor that can be sized to simulate a server computing device and can have multiple sensing equipment mounted inside of the air quality monitor. An enclosure of the air quality monitor can have a size and a shape that approximates a server computing device so as to accurately simulate the air inside of one or more co-located server computing devices. The size and shape of the enclosure of the air quality monitor can enable the air quality monitor to be mounted into one or more openings of a common server rack, such that the air quality monitor can be interspersed among server computing devices, in server racks, in a data center. The air quality monitor can comprise sensing equipment to detect corrosive aspects in the air. Such sensing equipment can include metallic members, such as corrosion classification coupons, made of various metals that are the same as the metals utilized by computing device hardware, such as the metals utilized for the traces of printed circuit boards (PCBs). The metallic members can be electrically coupled to a voltage source that can induce a current within the metallic members, thereby more accurately simulating the corrosion of actual, operating PCBs in the other computing devices. The air quality monitor can also comprise condensation sensing equipment to detect instances in which condensation can form on computing device hardware. Such sensing equipment can include condensation hosting members that can have a thermal mass that is approximately equal to the thermal mass of PCBs inside of server computing devices and other like computing hardware. Additionally, the condensation hosting members can include temperature sensors. Alternatively, or in addition, the condensation hosting members can comprise heating elements, such as thermos-resistors, by which the condensation hosting members can more accurately simulate the thermal effects and aspects of actual, operating PCBs in the other computing devices. Moisture detectors can detect the condensation on such PCB emulators, with such moisture detectors including electrical and optical moisture detectors. Additional aspects of the air quality monitor can include fans and air flow openings designed to simulate, within the air quality monitor, airflow analogous to that within other computing devices, such as server computing devices. Filters can be utilized to capture particulates and pressure differentiating sensors across such filters can quantify a particulate contamination of the air as would be inside of one or more server computing devices. Additionally, an off-gassing chamber can be included as part of the air quality monitor, which can receive materials whose off-gassing properties are to be evaluated.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Additional features and advantages will be made apparent from the following detailed description that proceeds with reference to the accompanying drawings.

DESCRIPTION OF THE DRAWINGS

The following detailed description may be best understood when taken in conjunction with the accompanying drawings, of which.

DETAILED DESCRIPTION

The following description relates to the monitoring of air quality inside of computing devices, such as rack-mounted blade server computing devices, utilizing an air quality monitor that can be sized to simulate a server computing device and can have multiple sensing equipment mounted inside of the air quality monitor. An enclosure of the air quality monitor can have a size and a shape that approximates a server computing device so as to accurately simulate the air inside of one or more co-located server computing devices. The size and shape of the enclosure of the air quality monitor can enable the air quality monitor to be mounted into one or more openings of a common server rack, such that the air quality monitor can be interspersed among server computing devices, in server racks, in a data center. The air quality monitor can comprise sensing equipment to detect corrosive aspects in the air. Such sensing equipment can include metallic members, such as corrosion classification coupons, made of various metals that are the same as the metals utilized by computing device hardware, such as the metals utilized for the traces of printed circuit boards (PCBs). The metallic members can be electrically coupled to a voltage source that can induce a current within the metallic members, thereby more accurately simulating the corrosion of actual, operating PCBs in the other computing devices. The air quality monitor can also comprise condensation sensing equipment to detect instances in which condensation can form on computing device hardware. Such sensing equipment can include condensation hosting members that can have a thermal mass that is approximately equal to the thermal mass of PCBs inside of server computing devices and other like computing hardware. Additionally, the condensation hosting members can include temperature sensors. Alternatively, or in addition, the condensation hosting members can comprise heating elements, such as thermos-resistors, by which the condensation hosting members can more accurately simulate the thermal effects and aspects of actual, operating PCBs in the other computing devices. Moisture detectors can detect the condensation on such PCB emulators, with such moisture detectors including electrical and optical moisture detectors. Additional aspects of the air quality monitor can include fans and air flow openings designed to simulate, within the air quality monitor, airflow analogous to that within other computing devices, such as server computing devices. Filters can be utilized to capture particulates and pressure differentiating sensors across such filters can quantify a particulate contamination of the air as would be inside of one or more server computing devices. Additionally, an off-gassing chamber can be included as part of the air quality monitor, which can receive materials whose off-gassing properties are to be evaluated.

Figure 1:
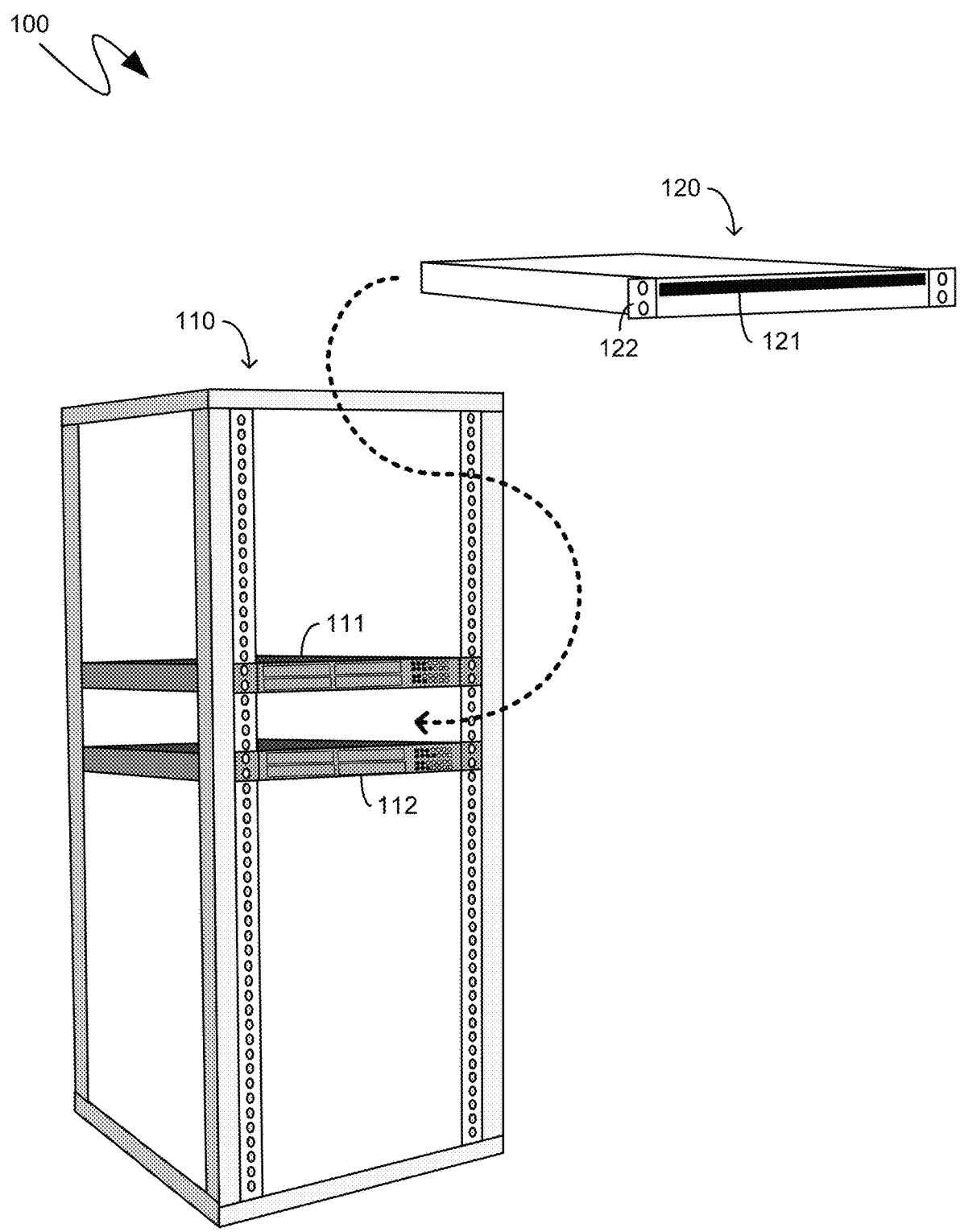
FIG. 1 is a diagram of an exemplary system providing a physical install context for an exemplary air quality monitor.

With reference to FIG. 1, an exemplary system 100 is illustrated, providing context for the descriptions below. The exemplary system 100 includes a server rack, such as the exemplary server rack 110. The exemplary server rack 110 can be any type of frame or support system that can accommodate and support multiple computing devices. For example, the exemplary server rack 110 can be a server rack conforming to various standards such as the EIA-310 standard, the IEC 60297 standard, and other like standards. As will be recognized by those skilled in the art, such standards typically define rack frames that are 19 or 23 inches wide and have mounting holes to accommodate equipment that is a multiple of approximately 1.75 inches high. Computing equipment designed to be mounted in such racks is often referenced based on the height of such equipment as being a multiple of the "rack unit", often abbreviated by the letter "U". Thus, for example, computing equipment can be referenced as being "1U", "2U", and so forth.

Typically, racks, such as exemplary server rack 110, house multiple computing devices, often in the context of larger computing environments such as datacenters comprising hundreds or thousands of such racks. The environmental conditions within such datacenters can be monitored, such as by sensors placed throughout the open space of a data center. However, the environmental conditions inside of computing devices mounted within such racks are not monitored. Accordingly, according to one aspect, an air quality monitor can comprise an enclosure, such as the exemplary enclosure 120, that is of approximately the same size and shape of other computing equipment mounted in, and supported by, a rack. As illustrated in FIG. 1, an exemplary enclosure for the air quality monitor can be in the form of a standard blade server computing device, such as by having a defined width and depth appropriate for the exemplary rack 110, and a height compatible with the spacing of the mounting holes. As one specific example, the exemplary enclosure 120 can be either 19 or 23 inches wide and deep, and can have a height of "1U" or "2U". Additionally, the exemplary enclosure 120 can comprise mounting hardware, such as the exemplary mounting hardware 122, which can be compatible with the mounting hardware of the rack, such as exemplary rack 110. For example, the spacing of the holes on the exemplary mounting hardware 122 can align with the holes of the exemplary server rack 110, such as by conforming with an appropriate standard. Other sizing for the exemplary enclosure 120 is equally contemplated so long as such sizing matches that of the computing devices whose internal air quality is to be monitored such that the exemplary enclosure 120 mimics, or simulates, a computing device in physical size.

As also illustrated by the exemplary system 100 of FIG. 1, according to one aspect, one or more air quality monitors can be installed into racks, such as the exemplary server rack 110, between various computing devices so that the atmospheric conditions experienced by the air quality monitor more accurately simulate and approximate those experienced by the computing devices themselves. For example, in the exemplary system 100 shown in FIG. 1, the exemplary enclosure 120 is illustrated as being mounted into the rack 110 between the exemplary computing devices 111 and 112 such that, for example, the exemplary computing device 111 is physically located above the exemplary enclosure 120, and the exemplary computing device 112 is located physically below the exemplary enclosure 120. In such a manner the sensors and equipment within the exemplary enclosure 120, namely those that comprise the other components of the aforementioned air quality monitor, can experience environmental conditions closely resembling those experienced by the internal components of the computing devices themselves, such as exemplary computing devices 111 and 112.

The exemplary enclosure 120 of an air quality monitor can include openings to facilitate airflow through the exemplary enclosure 120. For example, the exemplary enclosure 120 that is illustrated in FIG. 1 comprises a front opening 121 through which air can flow, or can be pulled through, such as with active air moving hardware mounted within the enclosure 120, such as one or more appropriately sized fans, or other like air moving hardware. Although not illustrated in FIG. 1, the exemplary enclosure 120 can comprise other openings, such as on an opposite side, namely the back side, of the enclosure 120 from the front air opening 121. Alternatively, or in addition, although again not illustrated in FIG. 1, the exemplary enclosure 120 can comprise openings on adjacent sides, such as on the top, bottom, or sides of the exemplary enclosure 120, to facilitate air movement within the enclosure 120 and more accurately simulate the environmental conditions found inside of computing devices, such as the exemplary computing devices 111 and 112.

Figure 2:
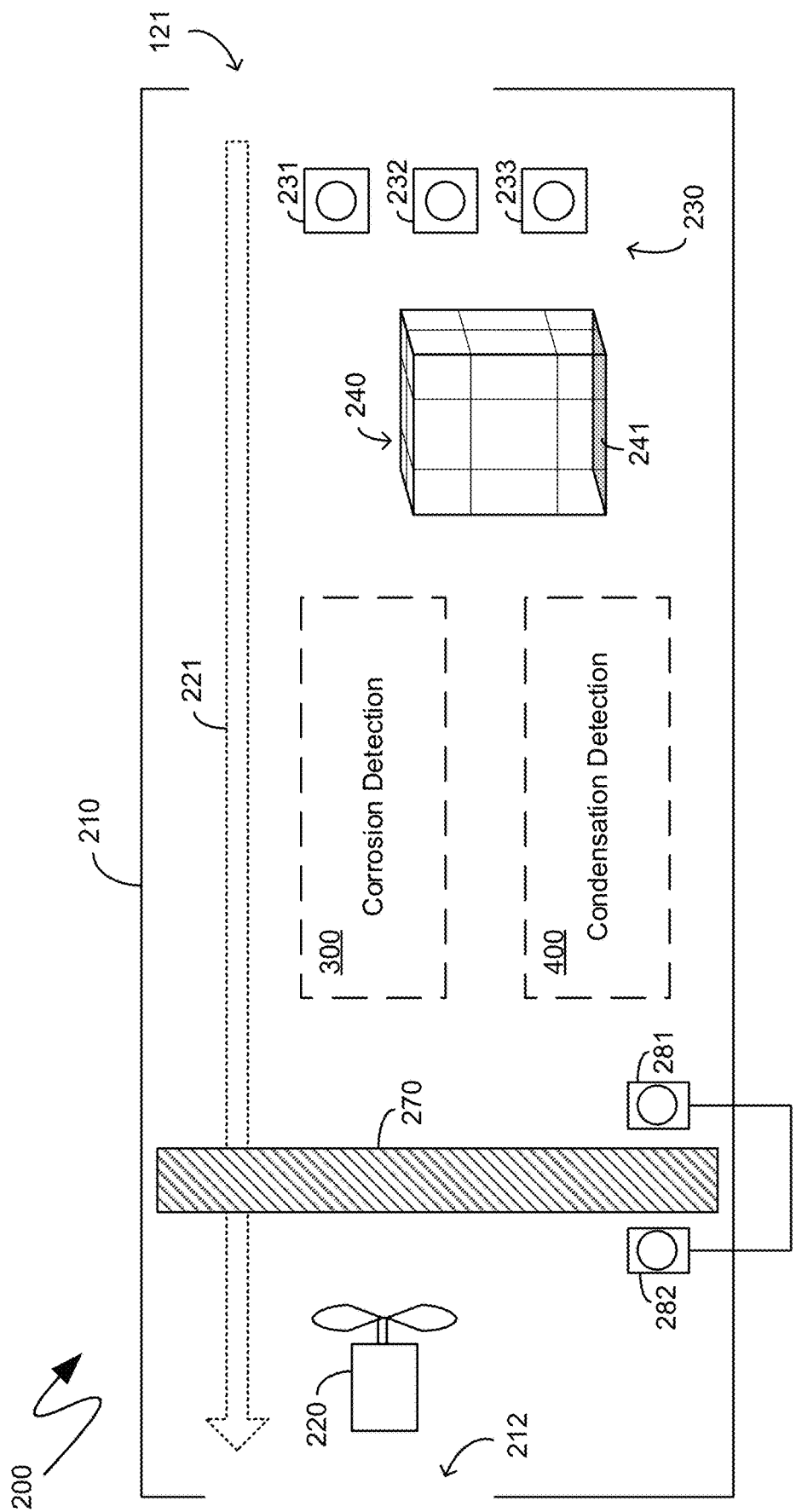
FIG. 2 is a diagram of an exemplary air quality monitor.

Turning to FIG. 2, the exemplary system 200 shown therein illustrates an exemplary air quality monitor 210 having the front opening 121 shown in FIG. 1, as well as a corresponding opening 212 on an opposite side of the enclosure. Air movement through the enclosure, such as exemplary air movement 221, can be facilitated by fans, such as the exemplary fan 220. As indicated previously, as an alternative, or in addition, to the opening 212, other openings can exist on adjacent sides, such as a top, bottom, or sides of the enclosure of the exemplary air quality monitor 210.

According to one aspect, the air quality monitor can comprise various sensors for detecting air quality and other like environmental conditions. For example, exemplary air quality monitor 210 can comprise various sensors 230 such as an exemplary dry bulb temperature sensor 231, an exemplary dew point sensor 232, and an exemplary relative humidity sensor 233. Other like moisture-based sensors can equally be installed within the enclosure and can be part of the exemplary air quality monitor 210. To detect particulates in the air, such as particulates carried in the airflow 221, a filter, such as the exemplary filter 270, can be installed within the airflow 221 and differential sensors, such as the exemplary differential sensors 281 and 282 can detect variances between the two sides of the exemplary filter 270. For example, the exemplary differential sensors 281 and 282 can detect a pressure differential between the front and back sides of the exemplary filter 270, nominated with reference to the exemplary airflow 221 such that, for example, a side of the filter 270 through which the exemplary airflow 221 enters can be considered a "front" side, while an opposite side of the filter 270, through which the exemplary airflow 221 exits, can be considered a "back" side. Such a pressure differential can indicate a quantity of particulates captured from the air by the exemplary filter 270. Accordingly, such a pressure differential can indicate a quantity of airborne particulates, such as would be experienced by the internal components of computing devices.

A quantity of particulates of a given size can be measured by changing the size of the openings of the exemplary filter 270. Thus, for example, a filter having larger openings can measure a quantity of larger airborne particulates, while a filter having smaller openings can measure a quantity of both larger and smaller airborne particulates. As will be recognized by those skilled in the art, filter opening sizes can be classified according to a "Minimum Efficiency Reporting Value" (MERV) classification. According to one aspect, appropriate filters for utilization within an air quality monitor 210, such as the exemplary filter 270 can have MERV values of 11, 12, 13, and other like MERV values.

To detect the effect of environmental factors on internal computer hardware, the exemplary air quality monitor 210 can comprise corrosion detection equipment, such as the exemplary corrosion detection system 300, and condensation detection equipment, such as exemplary condensation detection system 400.

In some instances, factors internal to computing devices can generate, or otherwise affect, corrosion, condensation, or other like effects on other internal computing hardware. For example, plastics utilized to coat wires, provide sound and/or temperature insulation, or provide physical cushioning and/or vibration resistance can generate gases, known as "off-gassing", that can have corrosive aspects, or can increase the corrosion being experienced by other internal computing hardware. Accordingly, according to one aspect, the exemplary air quality monitor 210 can comprise an off-gassing cage, such as the exemplary cage 240. The exemplary cage 240 can be mounted within the exemplary air quality monitor 210 and can be open to the airflow 221, such that the airflow 221 passes through the cage 240 and then exposes, at least those components of the exemplary air quality monitor 210 that are downstream in the exemplary airflow 211 to any off-gassing generated by samples placed within the cage 240. The exemplary cage 240 can comprise a platform 241 onto which samples, such as samples of wire insulation, vibration dampeners, thermal insulators, or any other like plastics or other materials whose off-gassing is to be tested, can be placed. The effects upon the corrosion detection system 300, condensation detection system 400, filter 270, and other like components can then be observed to detect off-gassing or other like undesirable environmental effects.

Figure 3:
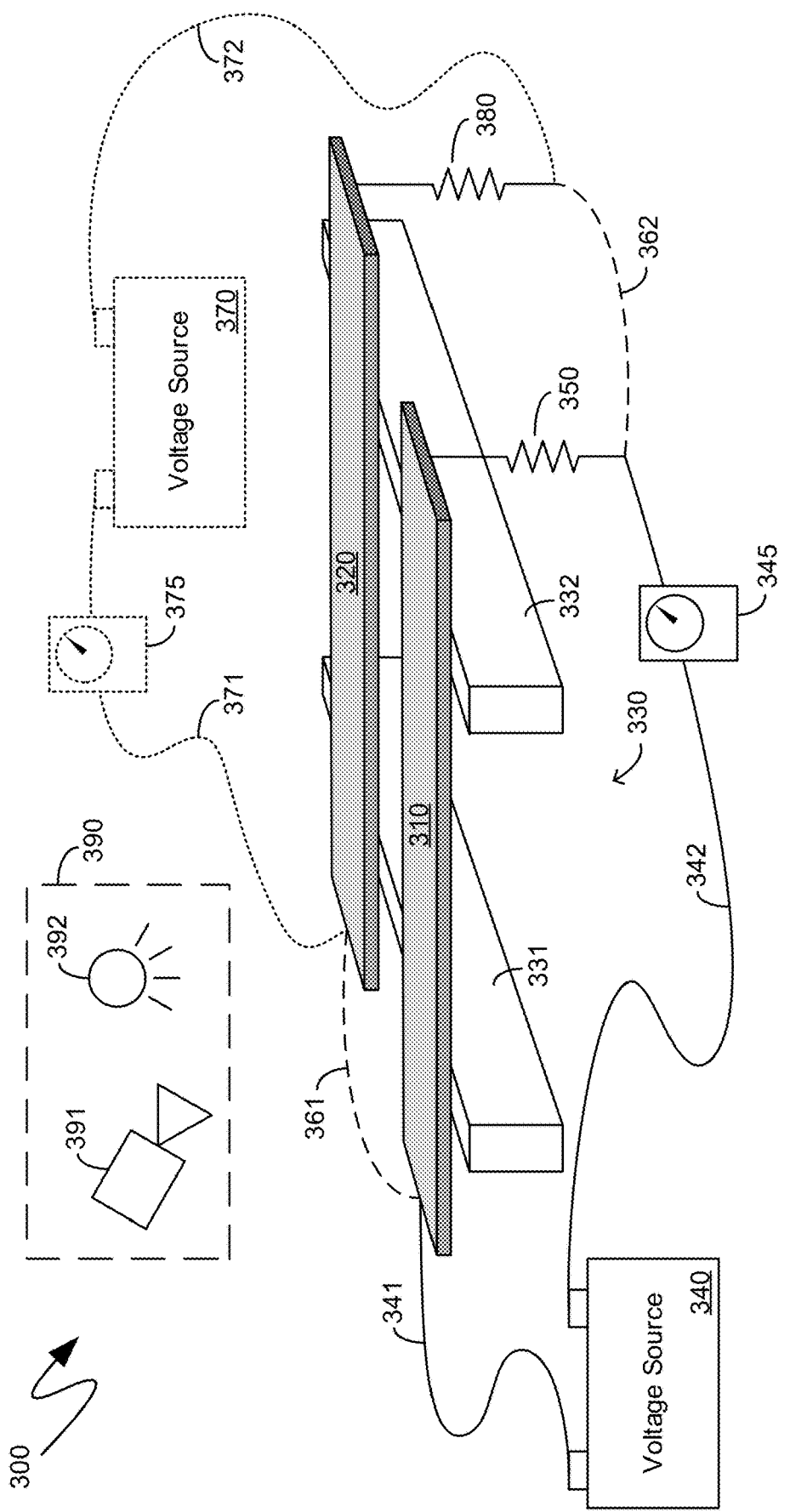
FIG. 3 is a diagram of an exemplary corrosion detection system of an exemplary air quality monitor.

Turning to FIG. 3, the exemplary corrosion detection system 300 illustrated therein comprises one or more corrosion hosting metallic members, such as the exemplary corrosion hosting metallic members 310 and 320. A corrosion hosting metallic member can be a material, typically metallic, whose corrosion is to be evaluated. For example, modern computing devices typically comprise Printed Circuit Boards (PCBs) whose traces include silver-based compounds. Accordingly, a corrosion hosting metallic member, such as exemplary corrosion hosting metallic number 310, can be silver to evaluate the corrosive impact, on silver, of the environmental conditions, such as the air quality, inside of a computing device, as simulated by the air quality monitor. As another example, modern computing devices often comprise copper wiring. Accordingly, a corrosion hosting metallic member, such as exemplary corrosion hosting metallic member 320, can be copper to evaluate the corrosive impact, on copper, of the environmental conditions inside of a computing device, as simulated by the air quality monitor. A common corrosion hosting metallic member is known in the art as a "Corrosion Classification Coupon" (CCC). As will be recognized by those skilled in the art, a CCC is a typically rectangular slab of metal having two sides, opposite each other, that each have a large surface area, while the remaining sides have substantially smaller surface areas. Other shapes, including oval, trapezoidal, and other like shapes of corrosion hosting metallic members are equally contemplated. Similarly, while thin, slabs of metal can be utilized, corrosion can equally be detected on cubic, spherical, and other like three-dimensional shapes that do not share the disproportionate surface areas of the slabs illustrated in FIG. 3. Thus, the illustrations in FIG. 3 of the contemplated corrosion hosting metallic members are meant to be exemplary and not limiting.

The exemplary corrosion detection system 300 shown in FIG. 3 can comprise support structures that can hold, retain, and otherwise support the corrosion hosting metallic members. By way of example, FIG. 3 illustrates an exemplary support structure 330 that can comprise two support members 331 and 332 onto which the corrosion hosting metallic members, such as the exemplary corrosion hosting metallic numbers 310 and 320, can be placed, affixed, held, or otherwise supported.

In some instances, the PCBs and other like components inside of computing hardware can be coated with protective coatings, sometimes referred to as "conformal coatings". The corrosive effects of the environment within such computing devices, as simulated by the air quality monitor, can be evaluated by applying such coatings to one or more of the corrosion hosting metallic members, such as exemplary corrosion hosting metallic members 310 and 320. Degradation of such coatings can be monitored through electric means, such as by detecting the absence of such coatings, due to corrosion, when an open circuit, or short circuit, is formed.

More specifically, two or more electrically conductive elements, such as thin wires, can be placed such that, for example, an electrical connection between the two wires is only prevented by the coating. Upon detecting the electrical connection, a determination can be made that the electrical connection came into existence due to the degradation of the coating, such as through corrosive effects. The detection of such an electrical connection can trigger a notification, or other like alarm, enabling administrators, or other like technicians, to physically remove the corrosion hosting metallic member and further evaluate the degradation of the coating. In a similar manner, an open circuit can be prevented by the existence of a coating, such that, upon detecting the open circuit, a determination can be made that the coating had degraded, such as through corrosive effects.

According to another aspect, a corrosion hosting metallic member, such as the exemplary corrosion hosting metallic member 320, can be comprised entirely of the coating, in order to determine the corrosive effects on the coating in the same manner as determining the corrosive effects on the, for example, silver or copper, described previously.

Because the metallic members of computing devices, such as the silver traces on PCBs, and the copper on copper wires, typically carry electrical current, an electrically inert corrosion hosting metallic member may not accurately simulate the corrosion that may be experienced by the hardware of computing devices. Consequently, according to one aspect, a voltage can be applied to one or more of the corrosion hosting metallic members to induce a current therein, thereby more accurately simulating the corrosive impact, on computer components, of the environment inside of computing devices. More specifically, the existence of a current through one or more of the corrosion hosting metallic members can result in, or can increase, electrochemical migration of some chemicals that can affect the corrosive forces being experienced.

Consequently, the exemplary corrosion detection system 300 shown in FIG. 3 is illustrated as comprising a voltage source, such as exemplary voltage source 340. The exemplary voltage source 340 can be a battery, such as is illustrated in FIG. 3, including rechargeable or non-rechargeable batteries of the various chemical makeups, or it can be an electronic power supply, such as a switching power supply, or other like power supply. The exemplary voltage source 340 can also be a current source in that the voltage output can vary while keeping the current output approximately constant. According to one aspect, exemplary voltage source 340 can be electrically coupled to a corrosion hosting metallic member, such as exemplary corrosion hosting metallic member 310, such as via the electrodes 341 and 342, thereby forming a closed circuit between the voltage source 340 and the exemplary corrosion hosting metallic member 310. While illustrated as electrode, exemplary electrode 342 can be accomplished by grounding both the exemplary voltage source 340 and the exemplary corrosion hosting metallic member 310. Additionally, a resistor, such as the exemplary resistor 350, can be connected, in series, such as is illustrated in FIG. 3, or in parallel, to further control the current generated in the exemplary corrosion hosting metallic member 310 by the exemplary voltage source 340.

The voltage source 340 can be a variable voltage source, thereby controlling the quantity of current generated in, for example, the corrosion hosting metallic member 310. Alternatively, or in addition, the resistor 350 can be a variable resistance resistor, thereby further controlling the quantity of current generated in the corrosion hosting metallic member 310.

If the air quality monitor comprises multiple corrosion hosting metallic members, such as the exemplary corrosion hosting metallic members 310 and 320, separate voltage sources can be provided for each corrosion hosting metallic member. Alternatively, two or more corrosion hosting metallic members can share a single voltage source. Thus, for example, the dashed lines 361 and 362 illustrate one alternative, namely electrodes that can electrically couple the corrosion hosting metallic member 320, and a corresponding resistor 380, in parallel with the corrosion hosting metallic member 310 and its corresponding resistor 350, as viewed by the single voltage source 340. The dashed lines illustrate that the electrodes 361 and 362 are one optional alternative. Another optional alternative, illustrated by the differently-dashed electrodes 371 and 372, and voltage source 370, provides the metallic member 320, and a corresponding resistor 380, with their own independent voltage source, namely the voltage source 370.

To detect corrosion on one or more of corrosion hosting metallic members, such as the exemplary corrosion hosting metallic members 310 and 320, a light-based corrosion detection system, such as the exemplary light-based corrosion detection system 390, can be positioned proximate to the exemplary corrosion hosting metallic members 310 and 320 and can be part of the exemplary corrosion detection system 300 shown in FIG. 3. A light-based corrosion detection system, such as the exemplary light-based corrosion detection system 390, can comprise a camera, such as the exemplary camera 391, which can be oriented towards some or all of one or more corrosion hosting metallic members. The exemplary camera 391 can be a visual-wavelength camera, an infra-red camera, an ultraviolet camera, an x-ray camera or any other light wavelength camera. The exemplary camera 391 can comprise multiple cameras, such as different ones of those enumerated, or can comprise multiple sensors, such as a visual-wavelength sensor and an infra-red sensor, within a single physical camera body. According to one aspect, in addition to one or more cameras, such as the exemplary camera 391, the exemplary light-based corrosion detection system 390 can also comprise one or more light sources, such as the exemplary light source 392. The exemplary light source 392 can provide light in a wavelength compatible with the camera 391, such as visual-wavelength light, infra-red light, ultraviolet light, x-ray light or any other light, or combinations thereof. The exemplary light-based corrosion detection system 390 can be communicationally coupled, such as through wired or wireless communicational couplings, with one or more recording or analysis computing devices so that images collected by the exemplary light-based corrosion detection system 390 can be remotely viewed and analyzed and, if appropriate, one or more notifications can be generated thereby.

Another mechanism by which to detect corrosion on one or more of corrosion hosting metallic members, such as the exemplary corrosion hosting metallic members 310 and 320, can be through conductivity testing. Thus, the exemplary corrosion detection system 300 shown in FIG. 3 can include an ammeter, such as the exemplary ammeter 345, or other like conductivity measuring device. If each of the exemplary corrosion hosting metallic members 310 and 320 is coupled to an independent voltage source, such as the exemplary voltage sources 340 and 370, then multiple conductivity measuring devices can likewise be included within the exemplary corrosion detection system 300 shown in FIG. 3. Thus, an exemplary conductivity measuring device 375, illustrated with dashed lines to again convey its optionality, can be coupled to the circuit formed by the exemplary additional voltage source 370, exemplary wires 371 and 372 and the exemplary corrosion hosting metallic member 320. As with the light-based corrosion detection system 390, conductivity devices, such as the exemplary devices 345 and 375, can also be communicationally coupled, either through wired or wireless couplings, with one or more remote devices, thereby enabling remote monitoring and detection.

Figure 4:
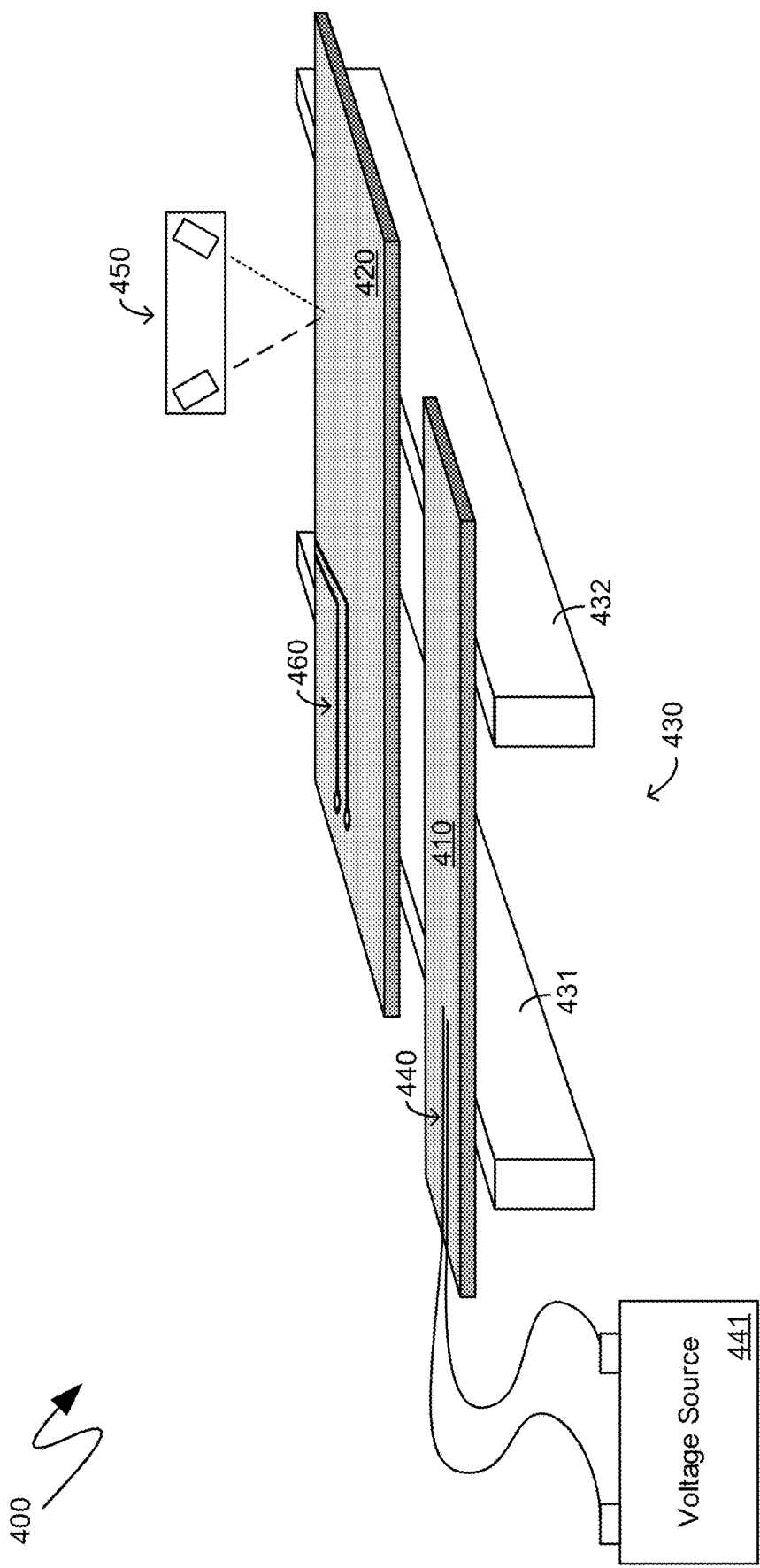
FIG. 4 is a diagram of an exemplary condensation detection system of an exemplary air quality monitor.

Turning to FIG. 4, the exemplary condensation hosting system 400 shown therein comprises one or more condensation hosting members, such as the exemplary condensation hosting members 410 and 420. According to one aspect, condensation hosting members can be selected based on their thermal mass. More specifically, the condensation hosting members can be selected to have a thermal mass approximating that of one or more PCBs, or other like computing hardware on which condensation may form, that are internal to computing devices. For example, the exemplary condensation hosting member 410 can be any material whose size and shape gives it an approximately equivalent thermal mass to that of, for example, a common PCB found in the computing devices that surround the air quality monitor in, for example the aforementioned rack.

In certain instances, the air temperature and humidity can change rapidly. In such instances, the thermal mass of PCBs can cause the temperature of those PCBs to change more slowly. For example, a change in the climate control mechanisms of a data center can result in a sudden rise in temperature of the air of the data center. Because of their thermal mass, the temperature of PCBs in computing devices can rise more slowly. During the intervening time, while the temperature of the PCBs is less than the air temperature, the temperature of the PCBs may be below the dewpoint of the now hotter data center air, causing condensation to form on the PCBs. To detect the formation of such condensation, condensation hosting members, such as the exemplary condensation hosting members 410 and 420, can have a thermal mass approximating that of the PCBs such that, if condensation is detected on the exemplary condensation hosting members, an empirically-accurate inference can be made that condensation also formed on the PCBs.

While any material, sized to have a thermal mass approximately equivalent to that of the PCBs, can be utilized, according to one aspect an actual PCB can be utilized as a condensation hosting member, such as exemplary condensation hosting member 420. The use of an actual PCB, with electrically functioning traces, can enable alternative moisture detection mechanisms, and other alternative detections, as detailed further below.

The exemplary condensation detection system 400 shown in FIG. 4 can comprise support structures that can hold, retain, and otherwise support the condensation hosting members. By way of example, FIG. 4 illustrates an exemplary support structure 430 that can comprise two support members 431 and 432 onto which the condensation hosting members, such as the exemplary condensation hosting numbers 310 and 320, can be placed, affixed, held, or otherwise supported.

One of moisture detection mechanism that can be utilized to detect condensation on a condensation hosting member can be a liquid detection rope, also called a "wet rope", which can comprise two closely spaced electrically conductive wires, such as thin wires, placed on a surface of a condensation hosting member, such as the exemplary condensation hosting member 410. The accumulation of condensation can cause a short circuit, or otherwise electrically couple the two otherwise electrically disjoint wires, through the electric conductive aspects of water, thereby enabling the detection of condensation. The exemplary wires 440 and corresponding voltage source 441 are meant to illustrate such a moisture detection mechanism.

Another moisture detection mechanism can be optically-based, as illustrated by the optically-based moisture detection sensor 450 shown in FIG. 4. More specifically, one optical component of the moisture detection sensor 450 can generate a visible, ultraviolet, infrared, or other like optically-detectable wavelength, which can be reflected off of the surface of a condensation hosting member, such as exemplary condensation hosting number 420. Another optical component of the moisture detection sensor 450 can detect the reflection of such an optically-detectable wavelength. Because of the refractive and reflective differences between water and the surface of the condensation hosting member, such as the exemplary condensation hosting member 420, the moisture detection sensor 450 can detect differences in the reflection of the optically-detectable wavelength, and can, thereby, detect moisture on the surface of the condensation hosting member 420.

As indicated previously, use of an actual PCB as a condensation hosting member, such as the exemplary condensation hosting member 420, can enable other moisture detection mechanisms. For example, rather than utilizing an independent sensor, two or more electrically conductive traces, such as exemplary traces 460, can be etched onto the PCB. As with the exemplary wires 440, the electrically conductive aspects of water can electrically couple the two exemplary traces 460, thereby enabling them to detect moisture in a manner analogous to that described above. As another example, traces, such as the exemplary traces 460, can be configured such that an open circuit, rather than the aforementioned short-circuit, can be indicative of moisture, such as in the form of condensation.

Yet another moisture detection mechanism can be based on salt, which can become electrically conductive in high humidity. Consequently, salt can be a basis for generating a short circuit, or an open circuit, such as in the manner described previously, in the presence of high humidity. Accordingly, salt can be utilized as a humidity sensor and/or as a moisture detection mechanism, or to aid one of the previously described moisture detection mechanisms.

As also indicated previously, PCBs can be coated with a protective coating, such as a conformal coating. Accordingly, condensation hosting members can be coated with the same coating to more accurately simulate actual PCBs in the computing devices. For example, the exemplary condensation hosting number 420, which, as indicated previously, can, itself, be a PCB, can be coated in a manner analogous to the actual PCBs in the computing devices. Such a coating can prevent moisture from forming the aforementioned short-circuit or open circuit. Thus, the presence of a short-circuit or open circuit can indicate, not only the presence of condensation, but also that over the time period evaluated, the coating has degraded, worn away, dissolved, or otherwise is no longer present. In such a manner, the thickness of a protective coating that can achieve the relevant quantity of protection, can be empirically determined. As will be recognized by those skilled in the art, such coatings can be expensive, such that a precise determination of an applicable thickness can be very valuable.

To more accurately simulate the thermal behavior of PCBs in functioning computing devices, a condensation hosting member, such as one or more of the exemplary condensation hosting members 410 and 420, can have heaters, such as thermos-resistors, embedded therein, installed on the surface, or otherwise included as part of the condensation hosting member. Activation of such heaters can simulate the heat generated by the circuitry of functioning PCBs, thereby enabling the condensation hosting member to more accurately simulate the functioning PCB.

Additionally, thermocouples, or other like temperature sensors, can be installed in, or otherwise included as part of one or more of the condensation hosting members. Such temperature sensors can more accurately track a calculated, or anticipated, change between ambient air temperature and PCB surface temperature when the air temperature, such as in a data center, increases suddenly.

According to one aspect, differences in the thermal behavior between a condensation hosting member and a PCB, or differences based on the heat generated by the circuitry of a functioning PCB, can be accommodated by varying a speed of one or more fans in the air quality monitor, thereby decreasing the airflow across the condensation hosting member, and, thereby, delaying the effect of ambient air upon the condensation hosting member.

Turning back to FIG. 2, although not explicitly illustrated, the exemplary air quality monitor 210 can include components to facilitate its communicational and data gathering capabilities. For example, the exemplary air quality monitor 210 can include data storage capability, such as in the form of volatile and/or non-volatile data storage that can be communicationally coupled to one or more of the sensors described above, and which can store historical sensor data. Additionally, the exemplary air quality monitor 210 can comprise data communication hardware, including wireless or wired networking hardware, to enable data from the sensors described above to be transmitted from the exemplary air quality monitor 210. Such data communication hardware can be compatible with the data communication hardware of one or more other computing devices, or data communication devices, that are also present on a rack in which the air quality monitor is installed.

As indicated previously, the voltage sources described above can be in the form of power supplies. According to one aspect, an air quality monitor, such as the exemplary air quality monitor 210, can comprise a single power supply that can output one or more direct-current voltages that can act as the above-described voltage sources, as well as supply power to one or more sensors, and the aforementioned data storage hardware and data communication hardware. Such a power supply can be connected to a data center power grid in a manner analogous to that utilized by the other computing devices that are also present on the rack within which the air quality monitor is installed.

According to one aspect, such a coupling to the data center power can also be utilized to provide input to harmonic power detection sensors, which can also be part of an exemplary air quality monitor. Similarly, air sniffers or other like direct detectors of airborne contaminants can be included as part of the air quality monitor.

In such a manner, the quality of air, and other like environmental aspects, inside of computing devices, such as the ubiquitous blade server computing devices, can be monitored by an air quality monitor that can simulate the environmental aspects within such computing devices and can comprise the relevant sensors and detection mechanisms. In such a manner data can be collected that can either be utilized to provide input to real-time control systems, or which can be utilized to identify subsequent correlations and causations between environmental effects and one or more hardware failures, clusters of hardware failures, or hardware failure categories.

The descriptions above include, as a first example an air quality monitor comprising: an enclosure having a size and shape mountable into one or more openings in a server rack, the enclosure comprising a first set of one or more airflow openings on a first side of the enclosure and second set of one or more airflow openings on a second side of the enclosure, the first and second sides being either opposite to one another or adjacent to one another; a first corrosion hosting metallic member mounted inside the enclosure; a first voltage source electrically coupled to the first corrosion hosting metallic member, wherein the electrical coupling of the first voltage source to the first corrosion hosting metallic member induces a first current in the first corrosion hosting metallic member, the first current modifying an attraction of chemical contaminants to the first corrosion hosting metallic member; a first condensation hosting member mounted inside the enclosure, the first condensation hosting member having a first thermal mass approximately equal to a printed circuit board thermal mass of one or more printed circuit boards of one or more server computing devices that are also mountable into the one or more openings in the server rack; a first moisture detector positioned on or proximate to the first condensation hosting member and detecting moisture formation on at least one surface of the first condensation hosting member; and one or more fans mounted proximate to the second set of one or more airflow openings on the second side of the enclosure, the one or more fans generating an airflow within the enclosure via the first set of one or more airflow openings and the second set of one or more airflow openings.

A second example is the air quality monitor of the first example, wherein the first corrosion hosting metallic member is a corrosion classification coupon.

A third example is the air quality monitor of the first example, wherein the enclosure has a height based on a whole multiple of a standard-defined rack unit measure (U).

A fourth example is the air quality monitor of the first example, wherein the first voltage source comprises a control that modifies an output voltage of the first voltage source.

A fifth example is the air quality monitor of the first example, further comprising a first resistor electrically coupled to the first corrosion hosting metallic member, wherein the first resistor, the first corrosion hosting metallic member and the first voltage source form a closed-loop circuit.

A sixth example is the air quality monitor of the first example, wherein the first corrosion hosting metallic member is one of: silver or copper.

A seventh example is the air quality monitor of the first example, further comprising: a second corrosion hosting metallic member; and one or more mounting rods onto which both the first and second corrosion hosting metallic members are mounted adjacent to one another along the one or more mounting rods.

An eighth example is the air quality monitor of the seventh example, wherein the first voltage source is also electrically coupled to the second corrosion hosting metallic member, the electrical coupling of the first voltage source to the second corrosion hosting metallic member inducing a second current in the second corrosion hosting metallic member, the second current modifying an attraction of chemical contaminants to the second corrosion hosting metallic member.

A ninth example is the air quality monitor of the first example, wherein the first corrosion hosting metallic member is coated with a printed circuit board conformal coating.

A tenth example is the air quality monitor of the first example, wherein the first moisture detector comprises thin wires and detects moisture based on electrical conductivity between the thin wires.

An eleventh example is the air quality monitor of the first example, wherein the first moisture detector comprises photoelectric sensors that detect moisture based on changes in reflectivity from the at least one surface of the first condensation hosting member.

A twelfth example is the air quality monitor of the first example, wherein the first condensation hosting member is a first printed circuit board.

A thirteenth example is the air quality monitor of the twelfth example, wherein the first printed circuit board is coated in a conformal coating and comprises closely spaced traces to detect degradation of the conformal coating through either an open circuit or a short circuit on the closely spaced traces.

A fourteenth example is the air quality monitor of the twelfth example, wherein the first moisture detector comprises closely spaced traces on the first printed circuit board to detect the moisture formation on the at least one surface of the first condensation hosting member through either an open circuit or a short circuit on the closely spaced traces.

A fifteenth example is the air quality monitor of the first example, further comprising: a cage, open to the airflow within the enclosure and mounted inside the enclosure, the cage comprising an off-gassing material support surface.

A sixteenth example is the air quality monitor of the first example, further comprising: a filter mounted within the airflow within the enclosure; a first sensor mounted proximate to a upstream airflow side of the filter; and a second sensor mounted proximate to a downstream airflow side of the filter; wherein the first and second sensor are communicationally coupled to detect a pressure differential across the filter.

A seventeenth example is the air quality monitor of the first example, wherein the first condensation hosting member comprises one or more thermocouples embedded inside to report a surface temperature of the first condensation hosting member.

An eighteenth example is the air quality monitor of the first example, wherein the first condensation hosting member comprises one or more electrical heating elements that generate heat when electrical current is flowed through the one or more electrical heating elements.

A nineteenth example is a server rack comprising: multiple server computing devices installed into the server rack; and an air quality monitor installed into the server rack between two of the multiple server computing devices, the air quality monitor comprising: an enclosure comprising a first set of one or more airflow openings on a first side of the enclosure and second set of one or more airflow openings on a second side of the enclosure, the first and second sides being either opposite to one another or adjacent to one another; a first corrosion hosting metallic member mounted inside the enclosure; a first voltage source electrically coupled to the first corrosion hosting metallic member, wherein the electrical coupling of the first voltage source to the first corrosion hosting metallic member induces a first current in the first corrosion hosting metallic member, the first current modifying an attraction of chemical contaminants to the first corrosion hosting metallic member; a first condensation hosting member mounted inside the enclosure, the first condensation hosting member having a first thermal mass approximately equal to a printed circuit board thermal mass of one or more printed circuit boards of the multiple server computing devices; a first moisture detector positioned on or proximate to the first condensation hosting member and detecting moisture formation on at least one surface of the first condensation hosting member; and one or more fans mounted proximate to the second set of one or more airflow openings on the second side of the enclosure, the one or more fans generating an airflow within the enclosure via the first set of one or more airflow openings and the second set of one or more airflow openings.

A twentieth example is a method of monitoring air quality inside of computing devices, the method comprising: installing an air quality monitor into a server rack between two server computing devices, the air quality monitor comprising: an enclosure comprising a first set of one or more airflow openings on a first side of the enclosure and second set of one or more airflow openings on a second side of the enclosure, the first and second sides being either opposite to one another or adjacent to one another; a first corrosion hosting metallic member mounted inside the enclosure; a first voltage source electrically coupled to the first corrosion hosting metallic member, wherein the electrical coupling of the first voltage source to the first corrosion hosting metallic member induces a first current in the first corrosion hosting metallic member, the first current modifying an attraction of chemical contaminants to the first corrosion hosting metallic member; a first condensation hosting member mounted inside the enclosure, the first condensation hosting member having a first thermal mass approximately equal to a printed circuit board thermal mass of one or more printed circuit boards of the two server computing devices; a first moisture detector positioned on or proximate to the first condensation hosting member and detecting moisture formation on at least one surface of the first condensation hosting member; and one or more fans mounted proximate to the second set of one or more airflow openings on the second side of the enclosure, the one or more fans generating an airflow within the enclosure via the first set of one or more airflow openings and the second set of one or more airflow openings.

As can be seen from the above descriptions, an air quality monitor for monitoring the air quality inside of computing equipment has been presented. In view of the many possible variations of the subject matter described herein, we claim as our invention all such embodiments as may come within the scope of the following claims and equivalents thereto.

We claim:

1. An air quality monitor comprising:
   an enclosure having a size and shape mountable into one or more openings in a server rack, the enclosure comprising a first set of one or more airflow openings on a first side of the enclosure and second set of one or more airflow openings on a second side of the enclosure, the first and second sides being either opposite to one another or adjacent to one another;
   a first corrosion hosting metallic member mounted inside the enclosure;
   a first voltage source electrically coupled to the first corrosion hosting metallic member, wherein the electrical coupling of the first voltage source to the first corrosion hosting metallic member induces a first current in the first corrosion hosting metallic member to simulate a corrosion of an operating printed circuit board in one or more server computing devices that are also mountable into the one or more openings in the server rack;
   a first condensation hosting member mounted inside the enclosure, the first condensation hosting member comprising a heater, the first condensation hosting member utilizing the heater to simulate a thermal behavior of the operating printed circuit board in the one or more server computing devices;
a first moisture detector positioned on or proximate to the first condensation hosting member and detecting moisture formation on at least one surface of the first condensation hosting member; and
one or more fans mounted proximate to the second set of one or more airflow openings on the second side of the enclosure, the one or more fans generating an airflow within the enclosure via the first set of one or more airflow openings and the second set of one or more airflow openings.

2. The air quality monitor of claim 1, wherein the first voltage source comprises a control that varies an output voltage of the first voltage source.

3. The air quality monitor of claim 1, further comprising a first resistor electrically coupled to the first corrosion hosting metallic member, wherein the first resistor, the first corrosion hosting metallic member and the first voltage source form a closed-loop circuit.

4. The air quality monitor of claim 1, wherein the first corrosion hosting metallic member is one of: silver or copper.

5. The air quality monitor of claim 1, further comprising:
a second corrosion hosting metallic member; and
one or more mounting rods onto which both the first and second corrosion hosting metallic members are mounted adjacent to one another along the one or more mounting rods.

6. The air quality monitor of claim 5, wherein the first voltage source is also electrically coupled to the second corrosion hosting metallic member, the electrical coupling of the first voltage source to the second corrosion hosting metallic member inducing a second current in the second corrosion hosting metallic member.

7. The air quality monitor of claim 1, wherein the first corrosion hosting metallic member is coated with a printed circuit board conformal coating.

8. The air quality monitor of claim 1, wherein the first moisture detector comprises thin wires and detects moisture based on electrical conductivity between the thin wires.

9. The air quality monitor of claim 1, wherein the first moisture detector comprises photoelectric sensors that detect moisture based on changes in reflectivity from the at least one surface of the first condensation hosting member.

10. The air quality monitor of claim 1, wherein the first condensation hosting member is a first printed circuit board, the first printed circuit board differing from the operating printed circuit board in the one or more server computing devices.

11. The air quality monitor of claim 10, wherein the first printed circuit board is coated in a conformal coating and comprises closely spaced traces to detect degradation of the conformal coating through either an open circuit or a short circuit on the closely spaced traces.

12. The air quality monitor of claim 10, wherein the first moisture detector comprises closely spaced traces on the first printed circuit board to detect the moisture formation on the at least one surface of the first condensation hosting member through either an open circuit or a short circuit on the closely spaced traces.

13. The air quality monitor of claim 1, further comprising:
a cage, open to the airflow within the enclosure and mounted inside the enclosure, the cage comprising an off-gassing material support surface.

14. The air quality monitor of claim 1, further comprising:
a filter mounted within the airflow within the enclosure;
a first sensor mounted proximate to an upstream airflow side of the filter; and
a second sensor mounted proximate to a downstream airflow side of the filter;
wherein the first and second sensor are communicationally coupled to detect a pressure differential across the filter.

15. The air quality monitor of claim 1, wherein the first condensation hosting member comprises one or more thermocouples embedded inside to report a surface temperature of the first condensation hosting member.

16. A server rack comprising:
multiple server computing devices installed into the server rack; and
an air quality monitor installed into the server rack between two of the multiple server computing devices, the air quality monitor comprising:
an enclosure comprising a first set of one or more airflow openings on a first side of the enclosure and second set of one or more airflow openings on a second side of the enclosure, the first and second sides being either opposite to one another or adjacent to one another;
a first corrosion hosting metallic member mounted inside the enclosure;
a first voltage source electrically coupled to the first corrosion hosting metallic member, wherein the electrical coupling of the first voltage source to the first corrosion hosting metallic member induces a first current in the first corrosion hosting metallic member to simulate a corrosion of an operating printed circuit board in one or more of the multiple server computing devices;
a first condensation hosting member mounted inside the enclosure, the first condensation hosting member comprising a heater, the first condensation hosting member utilizing the to simulate a thermal behavior of the operating printed circuit board in the of one or more of the multiple server computing devices;
a first moisture detector positioned on or proximate to the first condensation hosting member and detecting moisture formation on at least one surface of the first condensation hosting member; and
one or more fans mounted proximate to the second set of one or more airflow openings on the second side of the enclosure, the one or more fans generating an airflow within the enclosure via the first set of one or more airflow openings and the second set of one or more airflow openings.

17. A method of monitoring air quality inside of computing devices, the method comprising:
installing an air quality monitor into a server rack between two server computing devices, the air quality monitor comprising:
an enclosure comprising a first set of one or more airflow openings on a first side of the enclosure and second set of one or more airflow openings on a second side of the enclosure, the first and second sides being either opposite to one another or adjacent to one another;
a first corrosion hosting metallic member mounted inside the enclosure;
a first voltage source electrically coupled to the first corrosion hosting metallic member, wherein the electrical coupling of the first voltage source to the first corrosion hosting metallic member induces a first current in the first corrosion hosting metallic member to simulate a corrosion of an operating printed circuit board in at least one of the two server computing devices;

a first condensation hosting member mounted inside the enclosure, the first condensation hosting member comprising a heater, the first condensation hosting member utilizing the heater to simulate a thermal behavior of the operating printed circuit board in the at least one of the two server computing devices;

a first moisture detector positioned on or proximate to the first condensation hosting member and detecting moisture formation on at least one surface of the first condensation hosting member; and one or more fans mounted proximate to the second set of one or more airflow openings on the second side of the enclosure, the one or more fans generating an airflow within the enclosure via the first set of one or more airflow openings and the second set of one or more airflow openings.

18. The air quality monitor of claim 1, wherein the first condensation hosting member simulates the thermal behavior of the printed circuit board in part by having a first thermal mass approximately equal to the first printed circuit board.

19. The air quality monitor of claim 1, further comprising a fan control that varies a speed of at least some of the one or more fans to further the first condensation hosting member simulating the thermal behavior of the printed circuit board.

20. The air quality monitor of claim 1, wherein the heater is a thermo-resistor.

* * * * *